United States Patent [19]
Ishizawa et al.

[11] Patent Number: 6,107,810
[45] Date of Patent: Aug. 22, 2000

[54] ANALYZER WITH FUNCTION OF DETECTING LIQUID LEVEL

[75] Inventors: Masato Ishizawa; Nobuo Suzuki, both of Hitachinaka, Japan

[73] Assignee: Hitachi, Ltd., Tokyo, Japan

[21] Appl. No.: 08/971,902

[22] Filed: Nov. 17, 1997

[30] Foreign Application Priority Data

Nov. 19, 1996 [JP] Japan ................................. 8-307970

[51] Int. Cl.$^7$ .................................................. G01R 27/26
[52] U.S. Cl. ........................... 324/662; 324/686; 422/100
[58] Field of Search ..................... 324/662, 663, 324/671, 678, 686; 422/100; 73/304 C; 361/91

[56] References Cited

U.S. PATENT DOCUMENTS

| | | | |
|---|---|---|---|
| 4,586,104 | 4/1986 | Standler | 361/91 |
| 4,736,638 | 4/1988 | Okawa et al. | |
| 4,818,492 | 4/1989 | Shimizu | |
| 4,897,244 | 1/1990 | Wallace et al. | |
| 4,970,468 | 11/1990 | Ishizawa et al. | |
| 4,977,786 | 12/1990 | Davis | |
| 5,049,826 | 9/1991 | Sasao | |
| 5,365,783 | 11/1994 | Zweifel | 73/304 |
| 5,572,735 | 11/1996 | Tanikawa | 395/750 |
| 5,866,426 | 2/1999 | Ball | 436/54 |
| 5,897,837 | 4/1999 | Mizuno | 422/100 |

FOREIGN PATENT DOCUMENTS

| | | |
|---|---|---|
| 670497 | 6/1995 | European Pat. Off. |
| 42 03 638 | 12/1993 | Germany |
| 3-94164 | 4/1991 | Japan |
| 3-261864 | 11/1991 | Japan |

OTHER PUBLICATIONS

"A New Method for Low–Capacitance Probing", IEEE Transactions on Instrumentation and Measurement, vol. 42, No. 3, Jun. 1993, pp. 775–778, Alfonso Carlosena, Rafael Cabeza, and Luis Serrano.

*Primary Examiner*—Ernest Karlsen
*Assistant Examiner*—Anjan K. Deb
*Attorney, Agent, or Firm*—Mattingly, Stanger & Malur

[57] ABSTRACT

A liquid level detecting circuit is pattern-printed on a board. The liquid level detecting circuit has a pair of discharge elements and an electrostatic capacitance change detecting circuit. One of the discharge elements is grounded, and the other of the discharge elements is connected to a pipetting probe and the electrostatic capacitance change detecting circuit. When an extraneous noise signal such as a noise signal caused by static electricity charged on the surface of a container is input through the pipetting probe while the pipetting probe is being moved toward the container containing a liquid the liquid surface of which is to be detected, the extraneous noise signal is discharged to the ground through the pair of discharge elements to suppress the transmission of the noise signal to be transmitted to the electrostatic capacitance change detecting circuit. An inductance placed between the other discharge element and the electrostatic capacitance change detecting circuit promotes the discharge of the noise signal.

4 Claims, 3 Drawing Sheets

ANALYZER WITH FUNCTION OF DETECTING LIQUID LEVEL

BACKGROUND OF THE INVENTION

The present invention relates to an analyzer, and more particularly relates to an analyzer with a function for detecting a liquid level of a liquid when a sample or a reagent is being pipetted.

When body fluid samples such as blood, urine or the like are analyzed on analysis items to be inspected using an automatic analyzer, a movable pipetting probe is used to deliver liquid from a sample cup or a reagent bottle to a reaction container. As the pipetting probe is dipped deeper into the liquid to be delivered, an amount of the liquid attached onto the outer wall of the probe is increased and accordingly the contamination becomes larger. In order to reduce the dipped depth of the pipetting probe into the liquid as much as possible, a pipetting mechanism disclosed in, for example, U.S. Pat. No. 4,970,468 or U.S. Pat. No. 4,818,492 is used.

In the pipetting mechanism disclosed in U.S. Pat. No. 4,970,468 or U.S. Pat. No. 4,818,492, a pipetting probe is electrically connected to an electric circuit for detecting changes in electrostatic capacitance. When the pipetting probe is moved downward to a sample container or a reagent container and the probe is in contact with the liquid surface, the operation of moving the probe downward is stopped and then the liquid is sucked into the probe.

According to the inventors' experience, when a pipetting probe itself is also used as a liquid level detecting electrode and particularly the humidity of the atmosphere is low, an erroneous liquid level detecting signal is often output. Such an erroneous liquid level detection is estimated to be on the basis of the fact that the sample container and/or the reagent container are made of a non-conductive material such as plastic or glass.

SUMMARY OF THE INVENTION

An object of the present invention is to provide an analyzer construction capable of reducing the frequency of erroneous liquid level detection when detecting a liquid level using a pipetting probe even if the humidity of the atmosphere is low.

The present invention is applied to an analyzer comprising a device for pipetting a liquid from a first container to a second container using a pipetting probe, in which the pipetting probe also serves as an electrode for detecting a liquid level of a liquid in the first container and the contained substance in the second container is measured by a measuring means. The analyzer in accordance with the present invention comprises a holding means for holding the first container, the holding means being grounded; an electric circuit for detecting a change in electrostatic capacitance between the pipetting probe and the holding means; a pair of discharge elements arranged opposite to each other, one element of the pair of discharge elements being electrically grounded; and means for electrically connecting the pipetting probe and the electrostatic capacitance change detecting circuit through the other element of the pair of discharge elements.

DETAILED DESCRIPTION OF THE PREFERRED EMBODIMENTS

Figure 1:
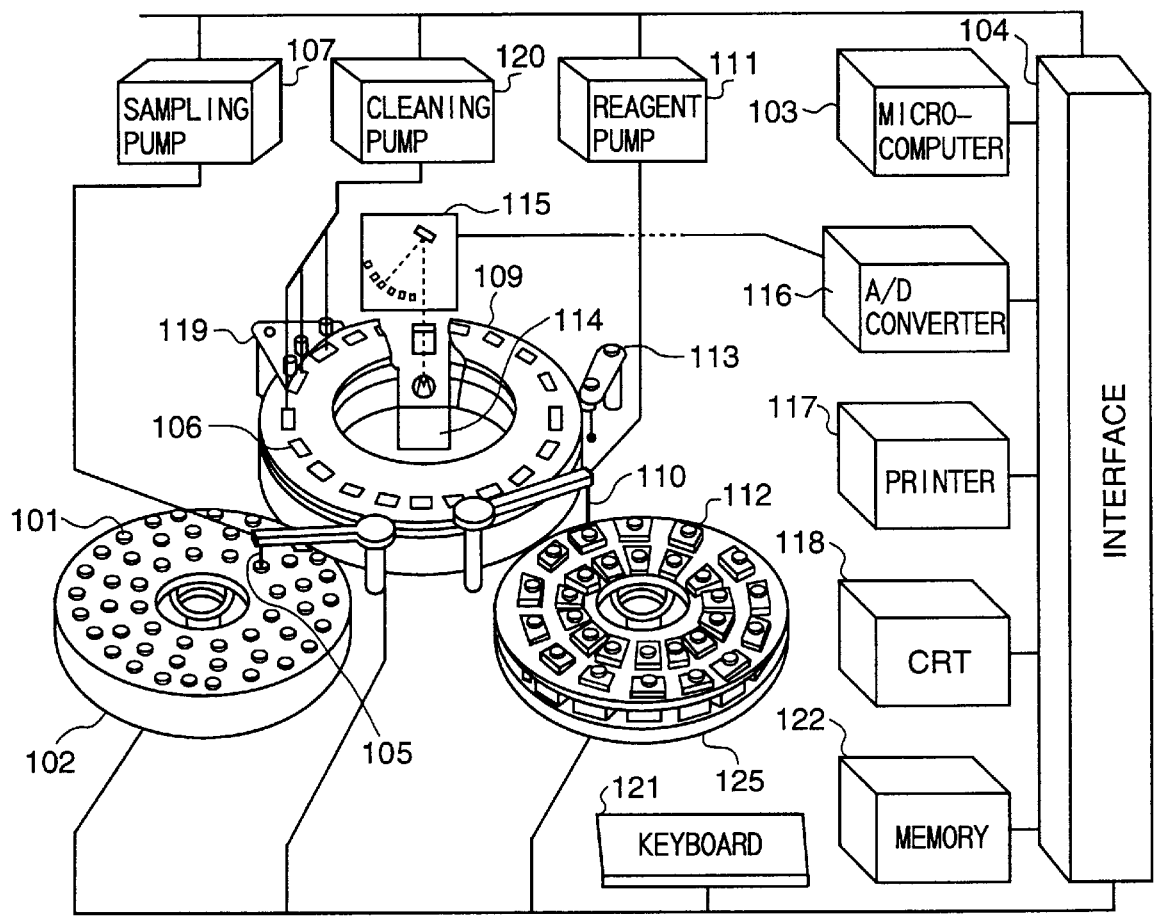
FIG. 1 is a schematic view showing the overall structure of an automatic analyzer to which the present invention is applied.

Referring to FIG. 1, a reaction disk 109 is rotatably arranged on a water bath kept at a constant temperature. Many reaction containers 106 are held in a circular form on the reaction disk 109, and transferred intermittently at a predetermined time interval. A sample pipetting probe 105 attached to a movable arm pipettes liquid samples from sample cups 101 arranged on a sample disk 102 to the reaction containers 106. On the other hand, a reagent pipetting probe 110 attached to the movable arm pipettes reagent solutions from reagent bottles 112 arranged on a reagent disk 125 to the reaction containers 106.

The sample pipetting probe 105 performs sucking operation and discharging operation of a liquid sample by operation of a sampling syringe pump 107. The reagent pipetting probe 110 performs sucking operation and discharging operation of a reagent solution by operation of a reagent syringe pump 111. Each of the pipetting probes 105 and 110 is made of a chemical-resistant metal, and also serves as a liquid level detecting electrode. Each of the pipetting probes 105 and 110 is electrically connected to a corresponding electrical detecting circuit. The sample disk 102 and the reagent disk 125 are respectively rotated so that a desired container is positioned at a liquid sucking position.

Analysis items to be analyzed for each sample are input from an input unit such as a keyboard 121. Operation of each unit in the apparatus is controlled by a computer 103.

The sample pipetting probe 105 is moved downward into the sample cup 101 transferred to the sample sucking position by the sample disk 102, the downward movement of the sample pipetting probe 105 is stopped when the lower end of the probe 105 is in contact with the liquid surface of the sample, and then a predetermined amount of the sample is delivered to the reaction container 106 by the probe 105. When the reaction container 106 containing the sample is transferred to a reagent adding position, a reagent solution corresponding to a specified analysis item is added by the reagent pipetting probe 110. Prior to such an addition of reagent, a predetermined amount of the reagent has been sucked in the probe 110 from a corresponding reagent bottle 112. In pipetting the sample and the reagent, the liquid level of the sample in the sample cup 101 and the liquid level of the reagent in the reagent bottle 112 are detected, and the downward moving operation of each probe is controlled corresponding to the detection of the liquid level.

The mixture of the sample and the reagent in the reaction container 106 is stirred at a position of an agitator 113. The reaction container 106 is passed through a light beam emitted from a light source 114 when the reaction container is transferred. At that time, an absorbance of the reaction solution is measured by a photometer 115 as a measuring means. The absorbance signal is input to the computer 103 through an A/D converter 116 and an interface 104, and then a concentration of the analysis item is calculated by the computer. The analyzed result is output to a printer 117 or displayed on the screen of a CRT 118 through the interface 104, and at the same time stored in a hard-disk 122 as a memory. The reaction container 106, after the photometric measurement, is washed at a position of a cleaning mechanism 119. A cleaning pump 120 supplies washing water to the reaction container and also discharges waste water from the reaction container.

Figure 2:
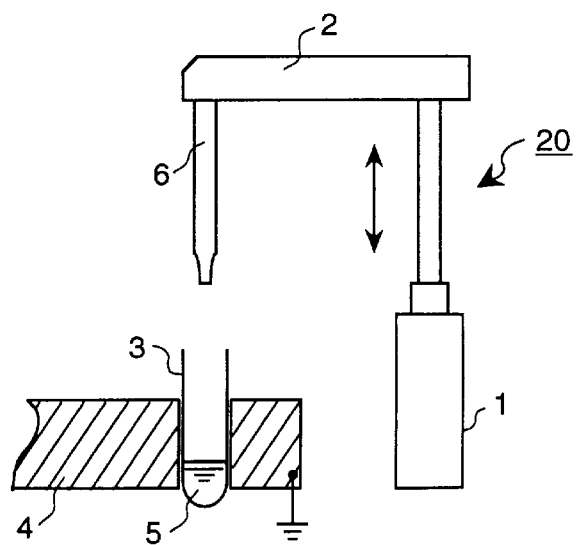
FIG. 2 is a view explaining the operation of a pipetting mechanism when a liquid level is detected.

With respect to the pipetting mechanism 20 in FIG. 2, a mechanism common to the sample pipetting mechanism and the reagent pipetting mechanism is shown.

Referring to FIG. 2, a container transfer holder 4 such as the sample disk or the reagent disk holds a container 3 containing a liquid 5 such as the sample or the reagent. The holder 4 has an electric conductive member, for example, a metallic member in a region surrounding the outer side wall of the container 3, and the electric conductive member is electrically grounded. That is, the holder 4 acts as an electrode of the liquid level detecting unit. The pipetting probe 6 for samples or reagents is attached to a movable arm 2 which is vertically movable and horizontally rotatable. The movable arm 2 is operated by a drive unit 1 controlled by the computer 103. When the pipetting probe 6 is moved downward and brought in contact with the liquid surface, the operation of moving the probe 6 downward is stopped and then a predetermined amount of the liquid is sucked into the probe 6.

Figure 3:
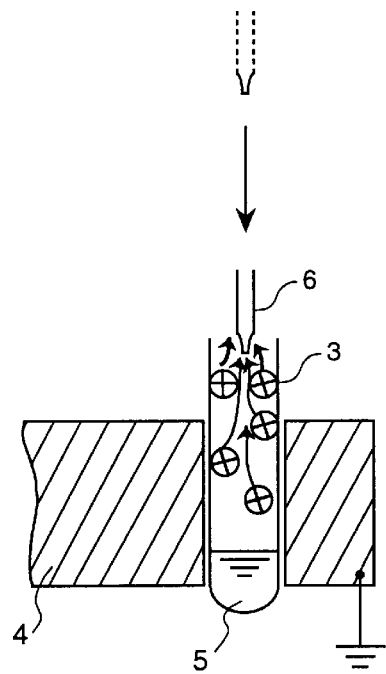
FIG. 3 is a view explaining an effect of extraneous noise associated with liquid level detection.

A phenomenon of picking-up extraneous noise will be described below, referring to FIG. 3. The containers 3 such as the sample cups 101 and the reagent bottles 112 are made of a non-conductive material such as glass or plastic. The pipetting probe 6 as a liquid level detecting electrode is made of a conductive material such as a metal. Since the container has a great resistance, static electricity is likely to be charged on the surface of the container particularly when the humidity of the atmosphere is low. The amount of charging-up due to the static electricity is larger in a plastic container than in a glass container. When the pipetting probe 6 is moved downward and becomes close to the container 3 charged with static electricity, the charged electricity is discharged to the probe 6.

Figure 5:
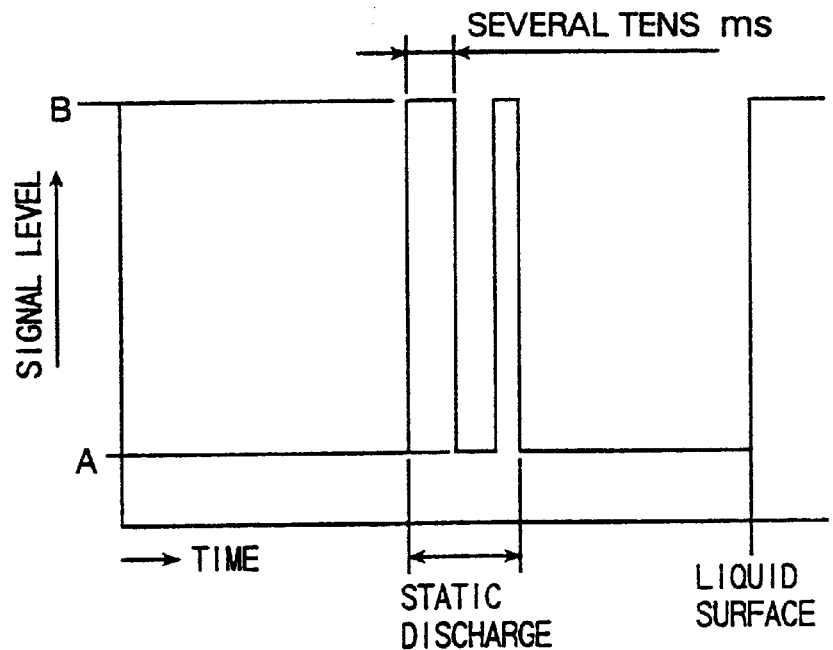
FIG. 5 is a chart showing an example of an extraneous noise signal when the present invention is not applied.

Such a discharge phenomenon occurs before the tip of the pipetting probe 6 is in contact with the liquid surface of the liquid 5. This discharge signal is detected by the electrostatic capacitance change detecting circuit electrically connected to the probe 6. FIG. 5 shows an example of such a discharging signal. The abscissa of FIG. 5 indicates the time of the pipetting probe 6 being moved downward which corresponds to the distance of the pipetting probe 6 being moved downward. The ordinate of FIG. 5 indicates the signal level, i.e., the intensity of the signal, and the level A indicates an undetectable level and the level B indicates a detectable level. Therefore, when such a discharge occurs, it is erroneously judged that the lower end of the pipetting probe 6 reaches the liquid surface though it does not reach the liquid surface yet.

Figure 4:
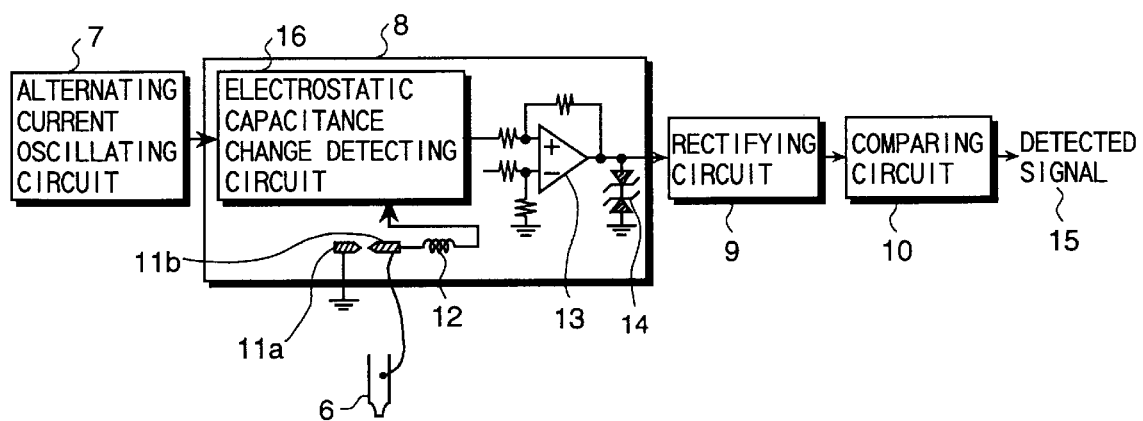
FIG. 4 is a block diagram explaining an electric system in a liquid level detecting unit applied to the analyzer of FIG. 1.

Each of the electric circuits in the liquid level detecting unit shown in FIG. 4 is pattern-printed on a board, but it is not limited to such a circuit. However, the pair of discharge elements 11a, 11b and the liquid detecting circuit 8 including the electrostatic capacitance change detecting circuit 16 are preferably formed by pattern printing. An alternating current signal output from an alternating current oscillator 7 is input to the liquid level detecting circuit 8 so as to detect the change in an electrostatic capacitance value detected thorough the probe 6. Although it is preferable that the alternating current wave is sinusoidal, a rectangular wave or a triangular wave may be used instead of the sinusoidal wave. The electrostatic capacitance change detecting circuit includes well-known electric circuits such as the bridge circuit disclosed, for example, in U.S. Pat. No. 4,818,492.

In the liquid level detecting circuit 8, the alternating current signal of the detected electrostatic capacitance change is amplified as it is, and the amplified signal is input to a rectifying circuit 9. In the rectifying circuit 9, the input alternating signal is converted to a direct current signal, and the direct current signal is input to a comparing circuit 10. In the comparing circuit 10, the input electrostatic capacitance change signal is compared with a value before change to obtain a detected signal 15 expressing the presence or absence of contact between the probe 6 and the liquid surface of the liquid in the container 3, that is, the presence or absence of the detected liquid level signal. The reason why the comparing circuit is operated by direct current signals is that the circuit can be simplified.

The pair of discharge elements 11a and 11b made of a conductive material on the board face each other through a gap of approximately 0.1 mm. The end in the facing side of each of the elements is point-shaped so that static electricity is concentrated there to discharge easily. The one discharge element 11a is electrically grounded. The other discharge element 11b is electrically connected to the pipetting probe 6 and also electrically connected to the electrostatic capacitance change detecting circuit 16.

In this way, the extraneous noise signal caused by the building of static electricity detected through the probe 6 is discharged to the ground through the discharge elements 11a, 11b, and consequently the transmission of the noise signal to the electrostatic capacitance change detecting circuit 16 is suppressed. Further, an inductance 12 is provided between the other discharge element 11b of the pair of discharge elements and the electrostatic capacitance change detecting circuit 16. The inductance 12 has a high impedance characteristic to a high frequency wave. By doing so, the noise signal is promoted to be discharged to the ground, and the transmission of the noise signal to the electrostatic capacitance change detecting circuit 16 is further suppressed. Accordingly, the probability of erroneous detection of the extraneous noise signal as a liquid level detection signal is substantially reduced.

The output signal of the electrostatic capacitance change detecting circuit 16 passes through an operational amplifier 13. An amplification factor of the operational amplifier 13 is generally several tens of times to several hundreds of times, though it depends on a minimum detecting capacitance of the apparatus. The output alternating current signal of the operational amplifier 13 is rectified by a rectifying circuit 9.

A conventional rectifying method generally converts an alternating current into a direct current by integrating the alternating current on the basis of capacitor discharge. However, since such a method integrates an instantaneous signal such as static electricity noises and other extraneous noises, an erroneous liquid surface level detection is likely to occur.

Figure 6:
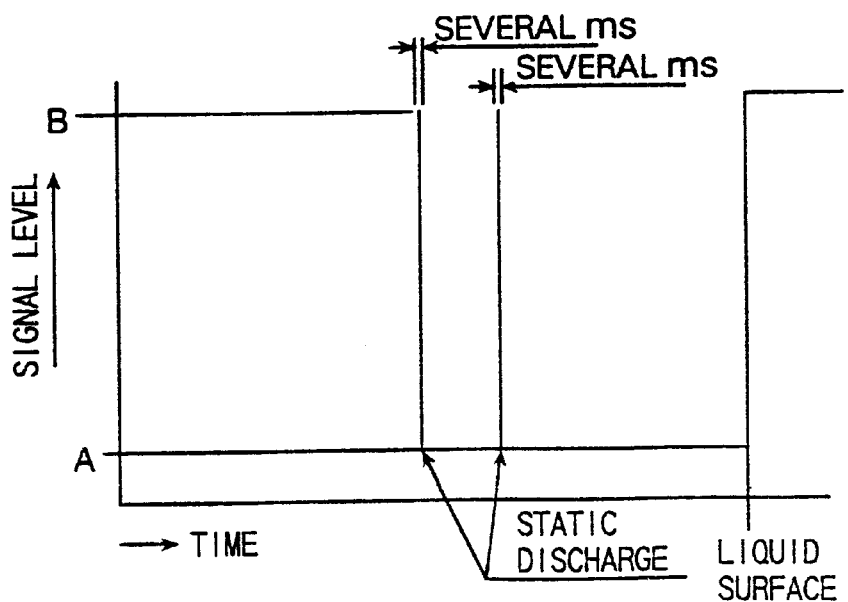
FIG. 6 is a chart showing an example in which an extraneous noise signal having the same signal level as that in FIG. 5 is reduced by applying the present invention.

On the other hand, in the example of the rectifying method shown in FIG. 4, since the output of the operational amplifier 13 in both the positive and negative directions is clamped by Zener diodes 14, an instantaneous signal such as static electricity noises and other extraneous noises, that is, an unnecessary signal is not integrated by being transmitted to the rectifying circuit 9. By constructing the circuits as shown in FIG. 4, when an amount of static electricity discharge from the surface of the container 3 is the same as in the example of FIG. 5, the width of the extraneous noise signal obtained in the electrostatic capacitance change detecting circuit 16 is reduced as shown in FIG. 6. Such a signal is not included in a detected signal 15 output from the comparing circuit 10 because it is not integrated. Consequently, it is possible to appropriately detect the electrostatic capacitance change which is produced when the pipetting probe 6 is bought in contact with the liquid surface. In the example of FIG. 5 where the present invention is not applied, the signal width of the extraneous noise is several tens of milliseconds. On the other hand, in the example of FIG. 6 where the present invention is applied, the signal width of the extraneous noise is reduced to several milliseconds or shorter.

What is claimed is:

1. An analyzer comprising a device for pipetting a liquid from a first container to a second container using a pipetting probe, said pipetting probe serving as an electrode for detecting a liquid level of the liquid in said first container, a contained substance in said second container being measured by a measuring means, the analyzer comprising:

holding means for holding said first container, said holding means being grounded, an electric circuit for detecting a change in electrostatic capacitance between said pipetting probe and said holding means;

a pair of discharge elements arranged opposite to each other, one element of said pair of discharge elements being electrically grounded; and means for electrically connecting said pipetting probe and said electrostatic capacitance change detecting circuit through the other element of said pair of discharge elements;

said pair of discharge elements preventing a noise signal from being transmitted from said first container to said electrostatic capacitance change detecting circuit when said pipetting probe approaches said first container.

2. An analyzer according to claim 1, wherein said pair of discharge elements individually have tips opposite to each other, each of said tips being point-shaped.

3. An analyzer according to claim 1, wherein said electrically connecting means further includes inductance means between said second element and said electrostatic capacitance change detecting circuit.

4. An analyzer according to claim 1, wherein said holding means comprises container transfer means for positioning said first container at a liquid sucking position.

* * * * *